(12) United States Patent
Weber

(10) Patent No.: US 6,203,540 B1
(45) Date of Patent: Mar. 20, 2001

(54) ULTRASOUND AND LASER FACE-LIFT AND BULBOUS LYSING DEVICE

(75) Inventor: Paul J. Weber, Ft. Lauderdale, FL (US)

(73) Assignee: Pearl I, LLC, Clearwater, FL (US)

( * ) Notice: Subject to any disclaimer, the term of this patent is extended or adjusted under 35 U.S.C. 154(b) by 0 days.

(21) Appl. No.: 09/085,948

(22) Filed: May 28, 1998

(51) Int. Cl.[7] ................................................. A61B 18/18
(52) U.S. Cl. ........................ 606/15; 3/11; 3/169; 604/22
(58) Field of Search ........................... 606/2–4, 9–11, 606/13, 15, 16, 27, 28, 32, 34, 40, 41, 49, 169; 604/22, 35, 19; 601/2

(56) References Cited

U.S. PATENT DOCUMENTS

| 5,015,227 | * | 5/1991 | Broadwin et al. . |
|---|---|---|---|
| 5,139,509 | * | 8/1992 | Fischer et al. . |
| 5,425,355 | * | 6/1995 | Kulick . |
| 5,655,547 | * | 8/1997 | Karni . |
| 5,693,043 | * | 12/1997 | Kittrell et al. . |
| 5,707,368 | * | 1/1998 | Cozean et al. . |
| 5,728,090 | * | 3/1998 | Martin et al. . |
| 5,755,714 | * | 5/1998 | Murhpy-Chutorian . |
| 5,776,092 | * | 7/1998 | Farin et al. . |
| 5,788,688 | * | 8/1998 | Bauer et al. . |

* cited by examiner

Primary Examiner—Linda C. M. Dvorak
Assistant Examiner—Bryan K. Yarnell

(57) ABSTRACT

A device for separating subcutaneous tissue and for tightening and contracting internal dermal tissue. In particular, the device uses an elongated hollow shaft having a distal end that has an ultrasonic energy source that projects ultrasonic energy outward at the distal end of the device to lyse through the subcutaneous fat tissue, and associated fiber optics and lens that projects laser beams outward to irradiate the internal dermal tissue.

16 Claims, 3 Drawing Sheets

ULTRASOUND AND LASER FACE-LIFT AND BULBOUS LYSING DEVICE

FIELD OF THE INVENTION

This invention relates to a device and method for contracting and tightening dermal or fibrous containing tissues of living beings. The device projects ultrasound to lyse through the internal tissue layers and lasers to irradiate the internal tissue. The method utilizes the device to enter the tissue through a small incision that may be less than 1 centimeter in length to lyse through the tissue layers, irradiate the internal dermal tissue and thereby cause contraction and tightening of the tissues.

BACKGROUND OF THE INVENTION

Traditionally, face-lifts are performed by surgically cutting and removing portions of the skin. In the subcutaneous tissue layer, where the fat joins the dermis, there are few nerves and there are only occasional blood vessels connecting the fat to the dermis. In the face, most of the blood flow moves horizontally as opposed to the other regions of the body where the blood flow moves vertically up into the dermis from the fat. This important fact of lateral blood flow allows the performance of a face-lift by cutting completely around the ear and separating the tissue out toward the mouth and lower neck and temporal regions.

No matter in what layer the fact-lift is performed, once sufficient tissues have been freed, stretched and pulled back toward the ear, excess tissue is then cut out with scissors or scalpel. The first reason a face-lift is successful is that the deeper tissues and surface tissues are freed and the tissues are then affixed to each other or other structures in order to tighten the tissues below the surface and indirectly on the surface. Secondly, surface tightening occurs when the tissue edges that remain following the removal of tissue are cut and sewn around the ear. Thirdly, tissue tightening occurs because of the trauma that occurs to most tissues during the entire procedure.

Whenever trauma occurs to tissue, scar tissue or fibrosis tissue is created. Scar/fibrous tissues have contractile elements in them, similar to miniature muscles. The key is to create the proper damage so that fibrous-tissue tightening may occur, but destruction, full thickness loss of tissue and overt scarification does not occur.

Improvements to the appearance of the epidermis also has been accomplished by use of lasers. Traditional laser resurfacing involves application of a Carbon Dioxide Laser on the epidermis destroying the epidermis and displaying the outer surface of the dermis. Erbium Yag Lasers are also used to tighten the skin and destroy the surface but do not cause as much thermal damage as Carbon Dioxide Lasers.

In the laser resurfacing procedure, superficial, medium, and relatively deep destruction methods are used depending upon the amount of resurfacing that a patient needs. Patients with mild sun damage may use superficial laser resurfacing procedures because most of the damage is near the top surface of the skin. Therefore, a high degree of concentration and destruction is not required. Patients with moderate or severe sun damage require relatively deeper laser resurfacing procedures, chemical peels or dermabrasion.

Laser resurfacing works very similarly to chemical peel or dermabrasion in that the surface of the skin is destroyed and new collagen is created. Epidermal elements, which coat the very surface of the skin, arise out of the hair pores. Too much destruction of the skin and too much destruction in general may destroy the hair pores and the ability of the skin to repopulate itself at the surface, which may lead to scarring. Scar tissue is fibrous tissue. Fibrous tissue makes up the bulk of the dermis, which is the "leather layer" of the skin. Whenever scar tissue is formed, these tissues in general contract.

The concept of the current invention by resurfacing skin from the "inside-out" was developed because of the nature of contraction observed when the interior or underside of the dermis tissue is damaged or altered by laser. The current invention projects laser beams on the interior surface of the dermis, which is the surface of the dermis that usually adjoins the subcutaneous fat tissue. The laser energy causes scarring and consequent contraction of the dermis.

The best age of the patient population suited to this invention are those without tremendous excess lack skin that would need to be cut out and thrown away during a traditional face-lift procedure. Patients that would benefit from this type of approach generally would be between the ages of 35 and 55.

Description of Prior Art

The use of ultrasonic medical therapy is well known in the art. Richards et al., U.S. Pat. No. 3,735,756, which is incorporated herein by reference, teaches such an ultrasonic use.

The term "laser" is an acronym for Light Amplification by Stimulated Emission of Radiation. As used herein, the term is meant to encompass a device which utilizes the principle of amplification of electromagnetic waves by stimulation emission of radiation to produce coherent radiation in the infrared, visible or ultraviolet region. Such radiation has been used in external medical applications, such as for cauterizing, for attaching detached retinas and for removing various skin cancers.

Zavislan et al., U.S. Pat. No. 5,653,706, which is incorporated herein by reference, teaches the use of laser energy for treatment of various sites under the skin. However, according to Zavislan, the interior sites are reached by projecting laser beams from outside the body through the epidermis, to the interior location.

Similarly, Karni, U.S. Pat. No. 5,655,547, which is incorporated herein by reference, teaches the use of lasers from a location exterior to the body to treat a location of the interior body.

Directing coherent radiation from a laser at a target is a well known method for precisely cutting that target by ablating or vaporizing a portion of it. When the target is living biological tissue, the dynamic nature of the target poses special problems. For example, fluids such as blood may flow into the area of the cut, obscuring that area and absorbing part of the energy that otherwise would go into ablating the target.

This problem can be mitigated by directing beams of coherent radiation of two or more wavelengths at the tissue, one beam to ablate the tissue and other to perform some other action, such as coagulating small blood vessels to prevent inflow of blood. For example, Freiberg, in U.S. Pat. No. 5,139,494, which is incorporated by reference for our purposes as if fully set forth herein, advocates using radiation in a range of wavelengths between about 0.1 and about 0.3 microns, and between about 2.0 and about 12.0 microns, for ablative cutting, and radiation in a range of wavelengths between about 0.3 microns and about 2.0 microns for coagulation. These beams of coherent radiation are directed coaxially at the tissue to be cut. Suitable means for combining laser beams coaxially are well known in the art. One such means is disclosed by Nakajima in U.S. Pat. No. 4,408,602. Another is disclosed by Jako in U.S. Pat. No. 4,503,854. Both of these patents are herein incorporated by reference for all purposes as if fully set forth herein.

Among the surgical procedures, to which laser surgery may be applied are skin resurfacing and hair implantation. In skin resurfacing, the upper layer of skin is ablated by a first laser beam while the underlying collagen is heated and shrunk by a second laser beam. In hair implantation, the accuracy of the drilling of holes of the implantation of new hair using a first beam is enhanced by the use of a second laser beam to coagulate small blood vessels and prevent inflow of blood. Both of these procedures are very delicate and require precise selection and control of the wavelengths, intensities and durations of the laser beams.

Karni provides a method for surgical alteration of skin tissue by simultaneous ablation, coagulation and shrinkage, comprising the steps of: (1) selecting a first coherent radiation source characterized by emitting a first coherent radiation having an extinction length in the skin tissue of between about 0.01 millimeters and about 0.001 millimeters; (b) selecting a second coherent radiation source characterized by emitting a second coherent radiation having an extinction length in the skin tissue of between about one millimeter and about 0.1 millimeters; (c) directing a first beam of the first coherent radiation at the skin tissue; and (d) directing a second beam of the second coherent radiation at the skin tissue, substantially coaxially and substantially simultaneously with the first beam.

Devices for medical treatment have been provided which use laser beams. Also handpieces from which laser beams are projected and manually traced over the skin, which may be compressed under glass slides for protection and heat dissipation purposes, are available. Such devices and treatment techniques generally use laser energy of a wavelength which makes it effective for treatment of lesions, because the lesions selectively absorb that wavelength. The general area containing the lesion is effectively flooded with generally collimated laser light of a wavelength that is highly absorbed by the lesion or the laser beam is moved over the area. Selective absorption of the laser light by the lesion is then responsible for photothermolysis. This technique is called selective photothermolysis and is discussed with respect to the skin in an article by R. R. Anderson and J. A. Parrish which appeared in *Science*, Vol. 220, p. 524, on Apr. 29, 1983. Also, the wavelengths of the laser illumination for selective photothermolysis are subject to scattering and diffusion of the skin. Accordingly, the area exposed to the radiation is heated and may be subject to collateral damage (i.e. reddened or even burned). This produces discomfort to patients and militates against the use of such laser treatment instruments and techniques.

Likewise, optical fibers have been used in a variety of medical applications. An optical fiber is a clad plastic or glass tube wherein the cladding is of a lower index of refraction than the core of the tube. When a plurality of such tubes are combined, a fiber optic bundle is produced. Optical fibers are flexible and are therefore capable of guiding light in a curved path defined by the placement of the fiber.

Fiber optic scopes have been developed for medical technology in order to enable illuminating and viewing access by the medical practitioner to the various interior parts of the body. In many medical applications, fiber optic devices have been combined with laser techniques to properly focus and apply laser radiation to interior parts of the body.

In addition, laser catheters have been constructed in which flexible or rigid hollow tubular devices (catheters) containing optical fibers are inserted into veins or arteries to illuminate internal parts of the body for diagnostic and surgical purposes. Such an application, in which fiber optic bundles are contained within a flexible catheter conduit, is described in U.S. Pat. No. 4,207,874 issued to D. S. J. Choy on Jun. 17, 1980. This fiber optic catheter contains a combination of: (1) a fiber optic viewing bundle; (2) a light source bundle for illuminating the region to be viewed; (3) a laser bundle for delivering laser light to the site for removal of tissue; (4) an annular space around the bundles for fluid supply or suction; and (5) a proximal supply and a transparent reservoir connected to the annular space.

Hakky et al., U.S. Pat. No. 5,312,399, which is incorporated herein by reference teaches a device that uses laser beams internally to remove selected organic tissue.

The use of internal laser energy for cosmetic surgery is taught by Keller in U.S. Pat. No. 5,370,642, which is incorporated herein by reference. Keller teaches a method of cosmetic surgery utilizing laser energy to incise, divide or resect tissue as necessary to perform a particular cosmetic surgical procedure. The use of laser energy instead of a scalpel greatly reduces the size of the incision necessary to perform cosmetic surgical procedures and also significantly diminishes the risk of complications. An endoscope with a channel for delivering the laser transmitting means can further reduce the size of the incision necessary to perform cosmetic surgical procedures.

Liss et al., in U.S. Pat. No. 4,724,835, which is incorporated herein by reference, teach the use of pulsed laser beams on injured cutaneous and subcutaneous tissue for therapeutic purposes. Digital circuitry provides the pulse train to activate the diode. Circuitry for detecting pulsed infrared energy is also taught.

The prior art to date, however, does not solve the problem of performing cosmetic surgery from interior body areas in a manner that affects the outer appearance of the body, while at the same time causing minimal or no scarring of the exterior tissue. In addition, the prior art does not teach the use of lasers in such a manner wherein the interior tissue is not destroyed, and is only minimally damaged. In addition, the prior art does teach the internal shrinkage of dermal tissue that is accessible internally only through small enclosed spaces and small incisions in the skin.

OBJECTS OF THE INVENTION

Accordingly, it is the general object of this invention to provide an device and a method of use which overcomes the disadvantages of the prior art.

It is a further object of this invention to provide an device and method of use which uses sonic energy to lyse through the subcutaneous layers of fat, projects laser beams on the interior side of the dermis and enables the contraction and tightening of dermal tissue from the inside-out.

It is still a further object of this invention to provide a device and a method for its use that attaches various types of lasers that can be delivered either by fiber-optic or micro articulation to the distal end of the advancing device that may be passed through the tissues to deliver the laser to distant sites with minimal incisions that can be less than one-centimeter in length about the ear and underneath the chin.

It is an additional object of this invention to provide a tissue contracting and lysing device and method for its use that has a rounded distal end and temperature regulators to reduce and eliminate collateral damage to internal tissues.

It is another object of this invention to provide a tissue contracting and lysing device and a method for its use that contains a suction means to remove internal steam, gases and tissues.

It is yet another object of this invention to provide a tissue contracting and lysing device and a method for its use that has a control panel on its handle to provide a fiber optic display, and to monitor and regulate temperature, laser power, suction, sonic energy and the like.

SUMMARY OF THE INVENTION

These and other objects of the instant invention are achieved by providing a device and a method for separating subcutaneous tissue and for tightening and contracting internal dermal tissue. In particular, the invention teaches the use of a device with an elongated hollow tube having a distal end that has a plurality of lumens extending therethrough, a source for generating at least one laser beam through one of the lumens, and a source for projecting ultrasonic energy through one of the openings at the distal end to lyse through openings and a plurality of lumens that extend through the tube to the openings in the distal end. The device also has an ultrasonic energy source that projects ultrasonic energy outward at the distal end of the device to lyse through the subcutaneous fat tissue, and a generating source for laser beams that projects laser beams through the openings outward to irradiate the internal dermal tissue. Optics at the opening or fiber tip disperse the laser energy to produce uniform illumination.

A method for separating subcutaneous tissue and tightening and contracting dermal tissue is also taught. The method comprises the steps of providing an incision into the skin of said patient and inserting the lysing elongated tube of the lysing device into the incision. Thereafter, the subcutaneous fat tissue is lysed utilizing ultrasonic energy so as to separate the dermis from the subcutaneous fat. Then at least one laser beam is directed to the site in need of contracting and tightening.

The method includes moving the elongated tube in a plurality of straight tracks diagonal from the point of incision, removing the elongated tube from the incision, and closing the incision.

In accordance with a preferred embodiment of the invention, the device includes a coagulation device to minimize bleeding from disrupted blood vessels, a fiber-optic or micro articulated laser so that the internal tissues can be viewed by the surgeon, a swan neck to increase maneuverability of the device, a bulbous distal end to minimize unintended damage to interior tissues, a suction lumen to remove internal steam, gasses and tissues, and a temperature moderator to prevent unintended burning of interior tissue.

DESCRIPTION OF THE PREFERRED EMBODIMENTS

Figure 1:
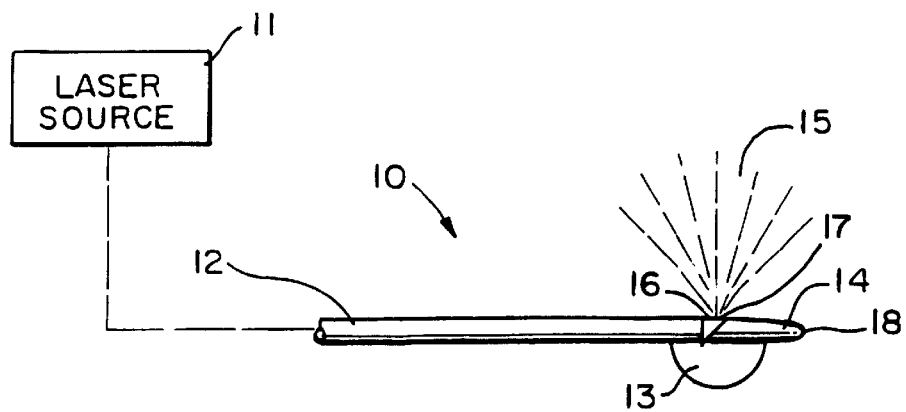
FIG. 1 is an elevational view of the device in a preferred embodiment.
Figure 2:
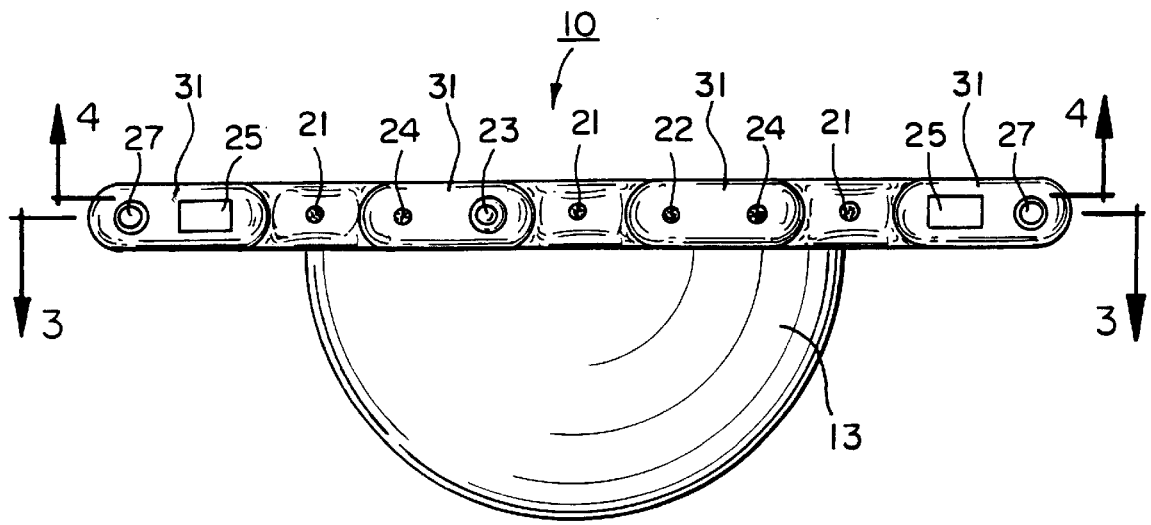
FIG. 2 is a frontal elevational view of a preferred embodiment of the device.
Figure 3:
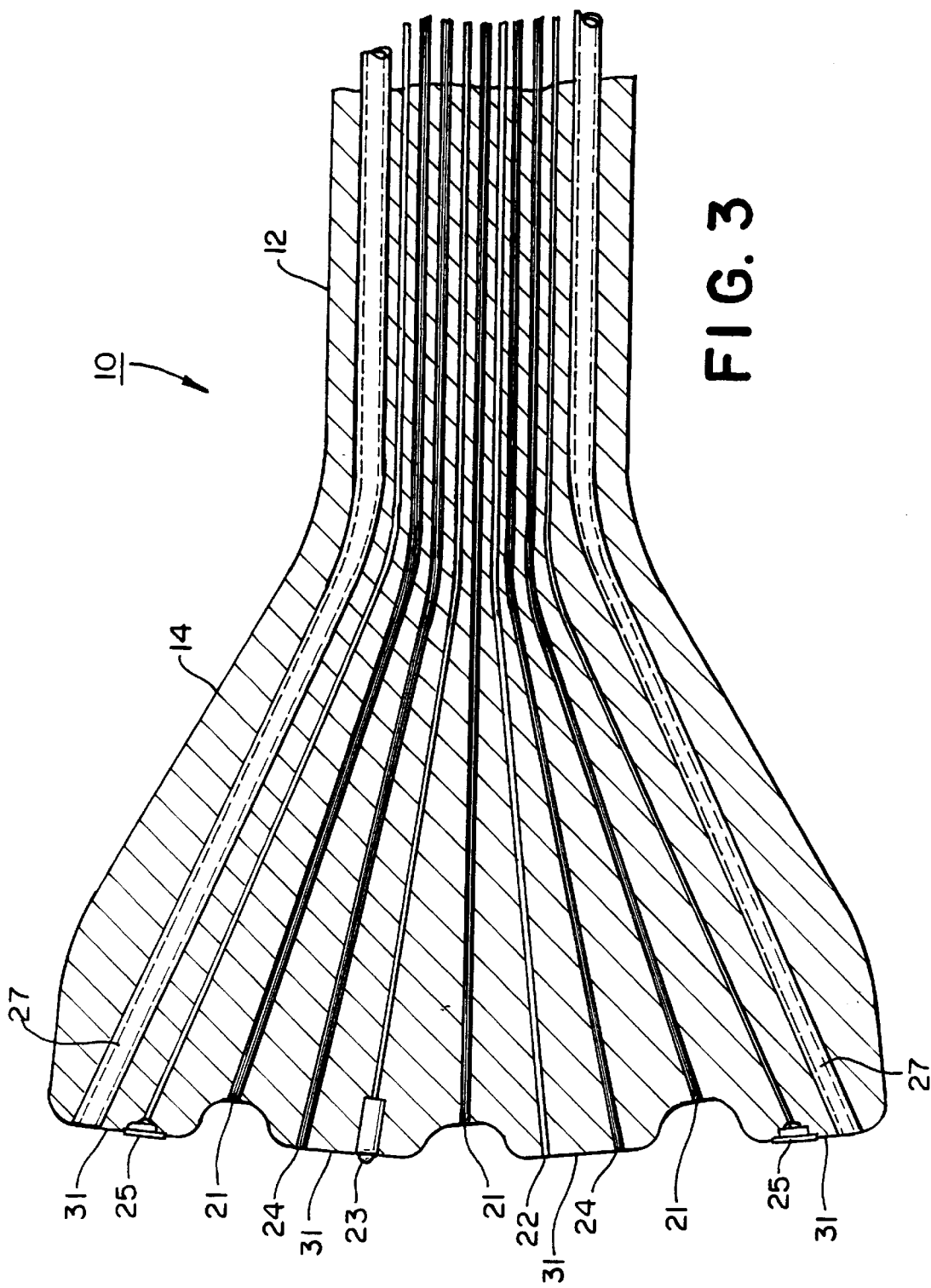
FIG. 3 is a cross-sectional view of the distal end of the device in a preferred embodiment.

Referring to FIG. 1, FIG. 2 and FIG. 3, there are illustrated embodiments of a laser and ultrasound bulbous lysing device 10 within the scope of the present invention. The lysing device 10 contains an elongated tube, 12, through which the laser energy from the laser source 11 may be transmitted by at least one transmitting fiber 21. The tube may also transmit ultrasound energy from an external or internal transducer (not shown) through a metal wire 22, or carry power to drive an ultrasound transducer at the tip.

Preferably, the distal end 14 of the lysing device 10 is curved to enable the device to lyse through layers of skin and fat tissue with minimal damage to the tissue. At the distal end 14, there is at least one bulbous structure 31 (FIG. 2), which separates the tissue layers while minimizing shearing forces or damage to the tissue.

The top of the elongated tube 12 contains an opening 17 through which an optical waveguide 16 emits laser beams 15. The optical waveguide 16 is connected to a laser transmitting fiber 21. When the device is moved between the skin and tissue layers in a direction that approximately parallels the tissue layers, the laser energy may be projected toward the underside of the dermis, thereby causing contraction of the skin tissue. The laser may be projected upward, forward or backward as long as it provides a means to heat the underside of the dermis.

In addition, the distal end 14 of the device contains a tip 18 through which ultrasound energy (not shown) is delivered in a forward direction. The tip is at the end of the metal wire 22 that is directly or indirectly connected to the ultrasound source (not shown). The ultrasound energy enables the device to lyse through the fat tissue just below the dermis tissue layer while causing minimal damage to muscles and arteries.

In another embodiment of the invention, the ultrasound is produced at the distal end 14 with a piezotransducer 13. Alternatively, the distal end may contain a cutting electrical current or high power laser.

The device also may be attached to at least one fiber-optic 23 in order to be able to observe the tissues and to determine whether blood vessels, bleeding and other problems have been encountered.

Referring now to FIG. 1, FIG. 2, FIG. 3 and FIG. 4, the device 10 in another embodiment also includes a means for effecting the illumination and visualization of the operative field while the device is in use. That means basically comprises a pair of optic fibers, 24 extending through a lumen. These fibers carry light from an external light source through the device and out their distal ends so that the light exiting therefrom illuminates the operative field or situs to the front and somewhat to the sides of the distal end of the device. Another optic fiber or bundle of fibers 23 also extends through the lumen for carrying the image of the operative field to a conventional telescope mounted on the device's frame. This allows the surgeon to visually observe the surgical procedure. The visual image is also preferably conveyed to some other optical viewing means, e.g., a video monitor (not shown) by monitoring a camera (not shown) on to the telescope's eye piece. The distal end of the optic fiber includes a lens (not shown) which directs the field of view of the fiber toward the direction of the laser beams.

In accordance with the preferred embodiment of the invention, the telescope is a conventional device such as an endoscope sold by Electro-Fiber Optic Corporation. The optic fiber bearing the image of the operative field is brought into the telescope where that image carried thereby can be seen by the surgeon looking into eye piece or can be displayed on the video monitor (not shown). The proximal end of the fibers terminate in a conventional light fitting which is arranged to be coupled to a cable bearing light from the light source. The telescope is mounted on to the frame so that it can be positioned at a desired location.

As mentioned earlier, the eye piece of the telescope is arranged to have a camera mounted thereon so that the image of the field within the patient's body can be displayed on a video monitor (not shown). Preferably that monitor is also connected to a color analyzer (not shown) which is capable of analyzing the color of the tissue as it is being treated. It has been found that the color of the tissue is a function of the depth and health of the tissue. By carefully monitoring the color, it possible to adjust the power (wattage) of the laser according to the type of tissue being lased.

In yet another embodiment of the invention, the distal end 14 contains at least one temperature sensor 25 to prevent burning of the tissue. In conjunction with the sensor, the distal end may further contain a cooling means to moderate the temperature of the device. Preferably, the cooling means would be an internal channel 26 containing a coolant that would circulate from outside the tube though the distal end and back. The coolant could consist of water, nitrogen gas, or the like.

In another embodiment, the distal end 14 contains surface temperature sensors 25. In yet another embodiment, the surface temperature sensors 25 are connected to a self regulating thermostat (not shown).

The distal end also may contain a suction means (not shown) to convey internal matter through at least one lumen 27 in the device 10 to an outer receptacle (not shown). The internal matter that might be suctioned could include steam, gas, tissue particles or the like.

The laser could be any of existing medical lasers but the preferred choice based on existing trials would be the Erbium Yag laser. The Erbium Yag operates at 2.94 $\mu$m and the per pulse energy would be in the range of 1.20 J/cm$^2$. For other lasers with lower absorption coefficients the per pulse energy can reach 100 J/cm$^2$. Alternatively, the laser is a YAG laser, sold by Laser Scope, Inc. under the model designation KTP/532.

In another embodiment, the laser beams would be pulsed to provide greater irradiation control.

Although $CO_2$ lasers are also currently used for skin resurfacing, the lack of a practical fiber optic which operates in this region makes it a poor candidate for this device.

In one embodiment, at least one lumen extends through the elongated portion of the instrument and carries an optic fiber 21 therethrough. The fiber would be from 100$\mu$ to 1000$\mu$ in diameter. An optical waveguide 16 is positioned at the free end of the optic fiber to disperse the laser beam into an array or continuous of beams 15. The fiber is provided to transmit laser light from a remote laser source, e.g., a YAG laser. The free end of the fiber is bent upward at an acute angle, e.g., 60 degrees or an angled mirror is coupled to the fiber end, to the longitudinal axis of the device, so that the laser light is directed therealong to exit somewhat laterally out of the distal end of the device into the tissue to be burned. Alternatively, the device could have a plurality of optic fibers 21 to transmit the laser energy.

In yet another embodiment, the distal end of the elongated tube 12 is open. In particular, the distal end of the tube includes a cut-away portion which opens approximately 180 degrees of the circumference of the tube at the top side of the distal end thereof, while the bottom of the distal end of that tube remains covered. The covered portion of the distal end of the sheath serves to shield a portion of the operative situs from the emerging laser beam. The laser may then be operated to project the laser beam upward so that it penetrates the interior dermal tissue on top of the device 10.

In another embodiment, the laser may also be used to coagulate blood vessels that are disturbed. In this embodiment, the laser light penetrates several millimeters, e.g., 1 to 3 mm, into the tissue to heat it, whereupon the tissue is coagulated. This action results in almost instantaneous hemostasis of that tissue and reduces, if not eliminates, bleeding.

Ultrasound delivered through the device emulsifies fat and/or other tissues at the shaped distal end. Although this device could operate from the near acoustic to 50 MHz, the preferred frequency will be near 20 Khz. This frequency is preferred because it maximizes emulsification of subcutaneous fat tissue, while minimizing the effects on muscle and arteries.

Figure 4:
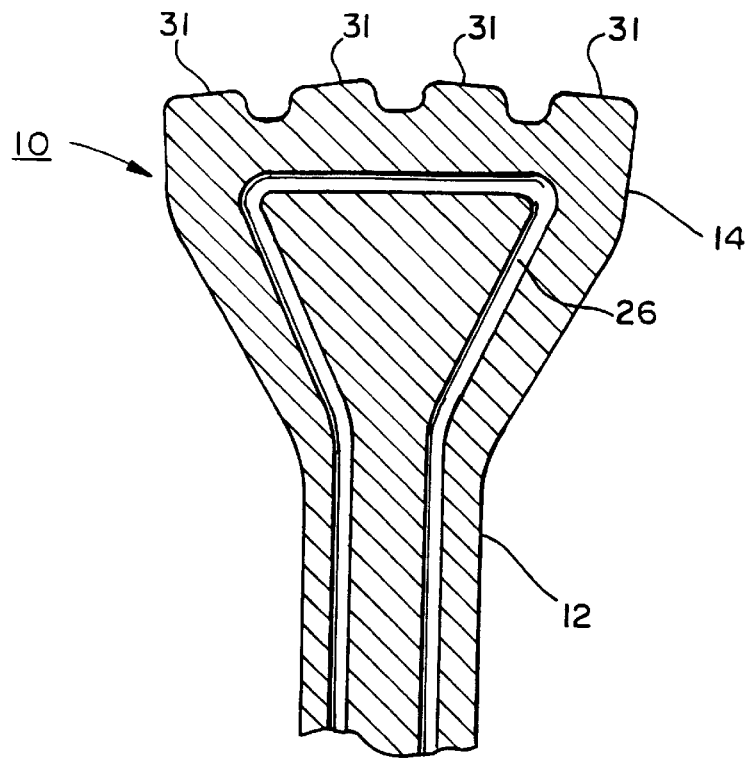
FIG. 4 is a cross-sectional view of the distal end of the device in a preferred embodiment.

Referring to FIG. 3 and FIG. 4, the distal end could be divided into a plurality of curved sub-distal ends 31. In this embodiment, the laser beams would be projected from fiber optics 21 that end at openings imbedded between the sub-distal ends. The location of the laser beam openings would prevent the heat surfaces surrounding the openings from contacting the internal tissue; consequently, preventing burning of the tissue.

Figure 5:
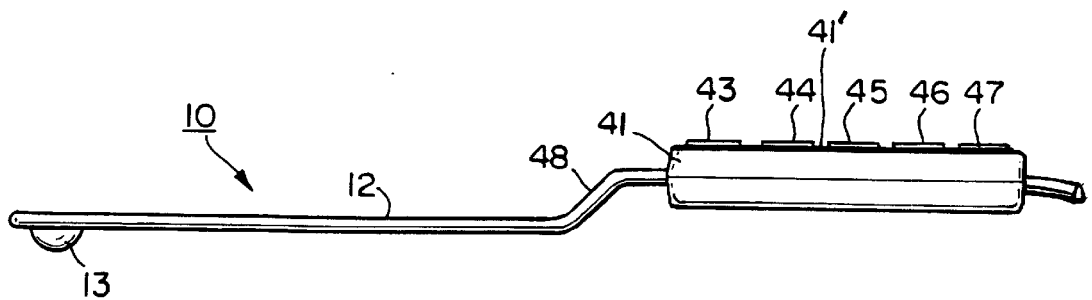
FIG. 5 is an elevational view of a preferred embodiment of the device.

Referring to FIG. 5, the device 10 includes an outwardly extending handle 41 arranged to be grasped in the hand of the surgeon so that the instrument can be supported and manipulated by the surgeon using only a single hand. The handle contains a display and control panel 41' for fiberoptics 43, distal end temperature 44, laser power 45, suction power 46, ultrasonic frequency 47 and the like. In yet another embodiment, the control panel could be controlled by voice commands. In yet another embodiment, the display could be in the control unit.

The elongated tube basically comprises a hollow tube preferably formed of fiber glass, plastic, or stainless steel, and approximately eight inches (20.3 cm) long.

In one embodiment of the invention, the elongated tube has a swan neck shape 48 for enhanced maneuverability of the device.

In another preferred embodiment of the invention, the laser transmitting fiber optics, metal wire, suction means, cooling sensor and cooling means each is housed in a separate lumen, thereby comprising a plurality of lumen.

In a preferred embodiment of the invention, a method for separating subcutaneous tissue and tightening and contracting dermal tissue in a patient is taught that comprises the steps of providing an incision into the skin of said patient and inserting the lysing elongated tube of the lysing device into the incision. Thereafter, the subcutaneous fat tissue is lysed utilizing ultrasonic energy so as to separate the dermis from the subcutaneous fat. Then at least one laser beam is directed to the site in need of contracting and tightening.

The method includes moving the elongated tube in a plurality of straight tracks diagonal from the point of incision, removing the elongated tube from the incision, and closing the incision. Preferably, the method is carried out in the face and neck region of the patient. The incision can be less than one centimeter in length made near the chin and alternatively near the neck.

In a preferred embodiment, the device will be moved in a track like fashion straight out at varying angles like the spokes of a wheel. The tracks will overlap closer to the central hub of the wheel, but a skilled surgeon will note that as the device is pulled up on the tissue, it will remain in a higher plane and the device may be pushed straight in order to again create the spoke effect. Once the interior underside of the dermis is heated, it will contract over the next several months. This will provide a tightening effect from the inside-out.

In another preferred embodiment, the method includes the step of evacuating steam or gas produced at the site of the lasing or irradiation.

In another embodiment, the method includes sensing the temperature at the site of irradiation.

In yet another preferred embodiment, the traditional surface laser procedure may also be used (simultaneously or later) in order to take up any small wrinkling or textural change that might be more noticeable on the surface. Traditional laser procedure could be performed at a date that is later than the internal laser procedure. Both procedures may be performed on the same day if there was an extremely superficial and low-energy use of the traditional laser procedure.

What is claimed is:

1. A device for separating fibrous dermis from subcutaneous fibrous tissue and tightening and contracting internal dermal tissue, an elongated hollow tube having a distal end, comprising said distal end comprising a lysing member consisting of bulbous and curved sub-distal ends in the same plane as said sub-distal ends;

a plurality of lumens, said lumens extending through said hollow tube and ending at said distal end of said tube and in the same plane as said sub-distal ends;

means for transmitting laser energy from a source of laser energy through at least one lumen to said distal end;

means for transmitting ultrasonic energy from a source of ultrasonic energy through at least one lumen to said distal end.

2. The device of claim 1 wherein said distal end further comprises a coagulation device.

3. The device of claim 1 wherein said laser is a fiber-optic laser.

4. The device of claim 1 wherein said laser is a micro articulated laser.

5. The device of claim 1 wherein said tube has a swan neck shape.

6. The device of claim 1 wherein said ultrasonic energy source is an ultrasonic resonator.

7. The device of claim 1 wherein said distal end further contains a cooling means.

8. The device of claim 1 wherein said generating source for laser beams is an Erbium Yag Laser.

9. The device of claim 8 wherein said laser operates at 2.94 $\mu$m.

10. The device of claim 8 wherein the per pulse energy from said laser is in the range of 1–20 J/cm$^2$.

11. The device of claim 1 wherein the per pulse energy from said laser is up to 100 J/cm$^2$.

12. The device of claim 1 wherein the ultrasound frequency is in the range of acoustic to 50 MHz.

13. The device of claim 1 wherein the ultrasound frequency is near 20 Khz.

14. The device of claim 1 further comprising a means for suction of internal matter substantially of steam and gases through one of said lumens.

15. The device of claim 14 further comprising a display and control panel for fiber-optics, distal end temperature, laser power suction power, and ultrasonic frequency.

16. The device of claim 1 further comprising a display and control panel for fiber-optics, distal end temperature, laser power, suction power, and ultrasonic frequency.

* * * * *